Figure 1:

United States Patent [19]

Lussi et al.

[11] Patent Number: 5,417,975
[45] Date of Patent: May 23, 1995

[54] CHEMICAL COMPOUND

[75] Inventors: Heinz Lussi, Chur; Peter Geistlich, Stansstad, both of Switzerland

[73] Assignee: Osteomedical Limited, Dublin, Ireland

[21] Appl. No.: 178,431

[22] Filed: Jan. 4, 1994

Related U.S. Application Data

[60] Continuation of Ser. No. 931,435, Aug. 19, 1992, abandoned, which is a division of Ser. No. 460,177, Apr. 2, 1990, Pat. No. 5,167,961.

[30] Foreign Application Priority Data

Jun. 2, 1988 [GB] United Kingdom ................. 8813033

[51] Int. Cl.⁶ ........................ A61K 9/14; A61K 47/42; A61K 37/12
[52] U.S. Cl. .................................... 424/423; 514/774; 530/353; 530/840; 623/16
[58] Field of Search .......................... 424/423; 623/16; 514/774; 530/353, 840

[56] References Cited

U.S. PATENT DOCUMENTS

| | | | |
|---|---|---|---|
| 4,596,574 | 6/1986 | Urist | 623/16 |
| 4,880,610 | 11/1989 | Constantz | 623/16 |

FOREIGN PATENT DOCUMENTS

| | | |
|---|---|---|
| 197693 | 3/1985 | European Pat. Off. . |
| 0182483 | 5/1986 | European Pat. Off. . |
| 0243178 | 10/1987 | European Pat. Off. . |
| 8901347 | 2/1989 | Germany . |
| 0004915 | 1/1982 | Japan . |
| 08058041 | 4/1983 | Japan . |
| 3125258 | 5/1988 | Japan . |
| 8607265 | 12/1986 | WIPO . |

OTHER PUBLICATIONS

Merck Index, entry 4276, p. 685.
Merck Index, entry 1701, p. 276.
Ganong, MD, *Review of Medical Physiology*, "A Lange Medical Book", 13th Ed. 1987, pp. 322–323.
Klinge et al., "Osseous Response to Implanted Natural Bone Mineral and Synthetic Hydroxylapatite Ceramic in the Repair of Experimental Skull Bone Defects," *J. Oral Maxillofac Surg.* 50:241–249, (1992).
Spector, M., "Analogs of Bone Mineral as Implants to Facilitate Bone Regeneration," *Proc. Portland Bone Symposium*, Jul. 21–24, 1993.

Primary Examiner—Thurman K. Page
Assistant Examiner—Carlos Azpuru
Attorney, Agent, or Firm—Rothwell, Figg, Ernst & Kurz

[57] ABSTRACT

The invention provides a process for the preparation of high purity bone mineral wherein the organic matter in degreased bone is degraded and solubilized by heating with ammonia or a primary amine, characterized in that the solubilized degradation products are extracted by washing with flowing water at temperatures below 60° C., such heating with primary amine and washing steps optionally being repeated, whereby substantially all organic matter removable by these steps is removed, the bone mineral so treated being heated in air at temperatures of up to 700° C.

4 Claims, 1 Drawing Sheet

CHEMICAL COMPOUND

This is a continuation of application Ser. No. 07/931,435, filed Aug. 19, 1992, now abandoned, which is a division of application Ser. No. 07/460,177, filed Apr. 2, 1990, now U.S. Pat. No. 5,167,961.

This invention relates to bone mineral products of large specific surface area.

Bones from slaughtered animals are an inexpensive raw material available in large quantities. They contain 50 to 60% of very fine crystallites of a form of hydroxylapatite bonded by collagenic tissue and containing significant qualities of proteinaceous and other matter as well as associated fat and muscle tissues. Such a hydroxylapatite, if it could be isolated in a pure state without changing its essential crystal structure, would represent a highly biocompatible remodelling bone implant material.

Natural bone mineral comprises hydroxyapatite-like crystallites with a particular degree of crystallinity, habit and size (irregular platelike morphology, 5–10 nm in thickness 10–50 nm in length) and surface chemistry resulting from the calcium to phosphate ratio (37.5–38.0% calcium and 15.5–5–19.0% phosphorus). The inorganic phase of bone contains porosity including ultrastructural interstices (10–100 nm) between the crystallities occuring naturally and produced by removal of the organic phase, and microscopic spaces (1–20 microns) including osteocyte lacunae, canaliculi, vascular channels, volkman's canals, and the canals of haversian systems (100–500 nm). The specific surface area, which is a measure of porosity is in the range 50 to 100 $m^2$/gm as determined by mercury porosimetry. The crystallinity of bone mineral can be characterized by X-ray diffraction and the porosity and crystallite morphology and size by electron microscopy. We have found that the composition and structure of natural bone mineral cannot be duplicated by calcium phosphate products formed *in vitro* or by naturally occurring hydroxyapatites prepared previously.

Hitherto two methods for the purification of natural bone mineral have been proposed namely calcination and solvent extraction.

The temperatures needed during calcination for the incineration of the organic constituents of the bones are rather high. This leads to extensive recrystallization of the mineral part with formation of much coarser crystals. The so formed material exhibits a small specific surface and is not superior to any chemically precipitated hydroxylapatite.

It should be emphasised that bone mineral which has been subjected to a treatment which results in significant increase in crystal size is much less readily remodelled on implantation since osteoclasts and osteoblasts cannot readily perform on such large crystals the dual function of mineral resorption and generation of new bone. Such implanted inserts may thus remain unchanged indefinitely, eventually giving rise to undesirable effects. On the other hand, many synthetic tricalcium phosphate products tend to be resorbed too rapidly for osteoblasts to regenerate new bone.

In the prior extraction process the proteins are extracted from degreased bone with a suitable solvent. The resulting bone mineral is then washed to remove the solvent.

Stegemann and Jung (Hoppe Seyler's Z. physiol. Chem. 320 (196) 272) used formamide for the protein extraction. This method proved to be impractical, the solvent being unstable under the conditions of hot extraction.

The sometimes recommended extraction with hot water instead of water washing after extraction was found to promote undesirable crystal growth (Skinner, Kempur and Pak: Calc. Tiss. Res. 10 (1972) 257).

The generally preferred method according to the prior art consists of the extraction of degreased bone with boiling ethylene diamine followed by washing with water. This method has been introduced by Williams and Irvine Jnr. (Science 119 (1954) 771) and later used by Losse and Hurley (Nature 177 (1956) 1032; Military Medicine (1957) 101) and by Kershaw (The Pharmaceutical Journal 190 (1963) 537). A patent for this process has been granted to Armour & Co. (U.S. Pat. No. 2,968,593 (1961)).

It has generally been claimed that extraction with ethylenediamine yields pure bone mineral. However, on repetition of this method we have always found that the products contain between 0.1% and 1% of organic residues, which can often lead to undesirable immunological response on implantation.

According to the present invention we provide a process for the preparation of high purity bone mineral wherein the organic matter in degreased bone is degraded and solubilised by heating with ammonia or a primary amine, characterised in that the solubilised degradation products are extracted by washing with flowing water at temperatures below 60° C., such heating with primary amine and washing steps optionally being repeated, whereby substantially all organic matter removable by these steps is removed, the bone mineral so treated being heated in air at temperatures between 250° C. and 600° C.

Some earlier methods tried to extract the bone protein with hot ethylene diamine without water washing. This method is not very effective. Following the present invention the degreased bones are treated with hot amines (or aqueous ammonia) to degrade and solubilize the originally insoluble proteins and the extraction of the solubilized degradation products takes place during washing with water.

We have found that this washing process is most important, since it not only causes the extraction of free soluble organics, but also the desorption of adsorbed degradation products. Due to the large specific surface of the bone mineral, adsorption is a very important effect preventing purification. Consequently washing with water has to be very extensive.

The final heating to some hundred degrees centigrade brings about further desorption. At the same time, remaining organic contaminants are at least partially destroyed by oxidation.

Because bone mineral exists in an extremely fine crystalline state, it is not very stable and is subject to recrystallization. All operating conditions must be selected to avoid undue crystal growth.

Any vertebrate bone can be used as the starting material for the present process. Bovine femur is a preferred raw material. The bones must be free from other tissues, such as marrow, cartilage or periosteum. Cortical as well as cancellous bone may be used in the process yielding macroscopically different types of end product. The bones must be ground or cut into pieces. The shape and size of the particles are generally determined by the requirements of the end product. Since all treatments are largely diffusion-controlled, finer comminution of the material facilitates the process.

The bones must substantially be completely degreased, since residual fats and their reaction products with amines will not readily be removed during the subsequent treatments. Degreasing is preferably performed by solvent extraction, suitable methods being known to those skilled in the art.

In general, degreasing can be effected by refluxing the bone material in the solvent which conveniently boils in the range 80° to 120° C., e.g. about 100° C. Suitable solvents include hydrocarbons such as toluene and methylcyclohexane.

Primary aliphatic or alicyclic amines are generally water soluble and are preferred as reagents for the protein degradation. These amines may possess more than one amine group per molecule and/or may contain other functional groups, e.g. hydroxyl groups. They preferably have 2 to 6 carbon atoms. Examples are cyclohexylamine, ethanolamine and ethylene diamine. Ammonia itself is also a suitable reagent. An addition of up to 50% water is often advantageous.

The degradation reaction may be performed by putting the degreased bone in a flask or vessel, adding enough reagent liquid to cover it and heating to a temperature between 80° C. and 200° C., preferably between 100° C. and 150° C. If ammonia or a low-boiling amine, such as ethylamine, is used, the reaction must be performed under pressure, preferably in an autoclave. Any more elaborate apparatus may also be used as long as the bone is in contact with hot reagent.

The duration of the heat treatment depends on the particle size of the bone, the reactivity of the amine and the reaction temperature, and may be between 2 and 200 hours. With bone pieces about 1 cm in diameter, using aqueous ethylene diamine as tile reagent and a reaction temperature of 118° C., a reaction time of 50 hours gives very satisfactory results.

After the degradation reaction the reagent, which now already contains a proportion of the degradation products, is drained off. The treated bone is transferred to a rinsing bath. After removal of most of the residual reagent the velocity of the continuous water-flow is adjusted to between 1 and 50 cm per hour, 10 cm/hour being a preferred velocity. A faster water-flow may be used, but this may not accelerate the process. To avoid recrystallization, the water temperature should not exceed 60° C. The water temperature should not, however, be unduly low if efficient extraction is to be achieved and is preferably above 10° C. A temperature of approximately 20° C. is preferred. The presence of amines in the washing water can easily be detected by pH measurement. Even after complete elimination of the reagent amine, desorbtion of degradation products still takes place. The washing process is therefore continued for 5 to 25 days, the duration depending largely on the particle size of the bone.

To achieve particularly high purity, the amine treatment and the washing must be repeated. When relatively large pieces of cortical bone are processed, repetition of the treatment may be necessary.

The final and essential step in the treatmeant of the bone mineral consists of dry heating to temperatures between 250° C. and 600° C., preferably not greater than 550° C., more preferably between 350° C. and 500° C., for several hours. The higher temperatures are more effective in removing contaminants but tend to increase the risk of recrystallization with consequent increase of crystal size. Heating in an oxygen-enriched atmosphere promotes the beneficial oxidation of organic residues.

The bone mineral produced by the process of the invention is a white, chalky, brittle material, showing the macrostructure of the original bone. On examination under the electron microscope, crystalline platelets no thicker than 100 Å units and 200 to 400 Å in diameter may be seen. By X-ray diffractography the presence of a hydroxylapatite lattice structure is confirmed. The width of the interferences is in agreement with the above-found crystal size. By mercury porosimetry a specific surface of 60 m$^2$ per g. has been measured.

The protein content is below the detection limit of the Lowry method (135 ppm) and the overall content of organic impurities is certainly below 150 ppm. In contrast, repetition of the methods described in the above literature shows that the products in general contain substantial contents of organic impurities, normally above 1000 ppm and often significantly more.

According to a further feature of the present invention we provide a bone mineral for use in medicine having substantially the crystal structure and mineral microstructure of natural bone permitting physiologically controlled, cell mediated remodelling on implantation, while having an organic impurity content below 150 parts per million. The bone mineral produced by the method of the invention shows, in fact, no organic impurities on electron microscopic examination at a magnification of 100,000.

In contrast to previously proposed natural or synthetic bone mineral materials, the product according to the invention is readily remodelled by the action of osteoclasts to effect resorption of bone mineral and the action of osteoblasts to produce new bone to eventually replace the implant.

The bone mineral according to the invention may thus be used as a remodelling implant or prosthetic bone replacement, for example in orthopaedic surgery, including hip revisions, replacement of bone loss e.g. in traumatology, remodelling in maxillo facial surgery or filling periodontal defects and tooth extraction sockets. In this context, the bone mineral may have adsorbed or absorbed therein one or more physiologically active substances.

Physiologically active substances which may be absorbed onto the bone mineral are preferably at least partially water-soluble and include antibacterial substances such as antibiotics, e.g. penicillins, cephalosporins, aminoglycosides etc., sulphonamides and, in particular, condensation products of formaldehyde with taurinamide or N-substituted taurinamide. The latter compounds may be represented by the formula

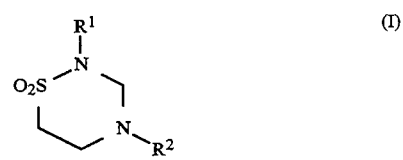

where $R^1$ is hydrogen or a $C_{1-4}$ alkyl group and $R^2$ is hydrogen or a group of the formula

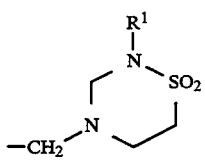

wherein $R^1$ has the above meaning.

The compound of formula (I) in which $R^1$ and $R^2$ are both hydrogen is taurultam while the compound in which $R^1$ is hydrogen and $R^2$ has the formula (II) is taurolidine. These compounds act as methylol transfer agents and are effective not only in destroying both gram negative and gram positive bacteria but also in inactivating both endotoxins and exotoxins produced by the bacteria.

Other useful physiologically active substances include proteins and polypeptides capable of assisting bone regeneration especially non-collagenous proteins derived from bone matrix and bone cells. These include mitogenic factors such as skeletal growth factor and morphogenic and angiogenic factors as well as transforming growth factors, $\alpha$ and $\beta$ types 1 and/or 2. Type 2 is especially important.

It has been found that while it is important in most instances to avoid significant modification of the size of the bone mineral crystallites, in order to ensure that the bone pieces when implanted, are readily converted into natural bone, there are certain environments, notably the highly vascularised maxillo facial region, where there may be some benefit in slight modification of the structure of the bone mineral to delay unduly rapid resorption. We have found that in this context it may be beneficial to increase the temperature of the final heating step to above 600° C., namely to a temperature between 600° and 700° C. Over this temperature range, there is modest increase in crystal platelet size and an increase in pore size. It is possible in this way to provide the surgeon with a range of bone mineral prosthetic products having different physical and physiological properties, by varying the temperature of the final heating step.

The following Examples are given by way of illustration only:

Example 1

Preparation of Degreased Bone

Femurs of freshly slaughtered cattle are sawed into slices 1 cm thick. These slices are cleaned by repeated boiling in water and by cutting off appending soft tissues. The material is dried at 100° C. in a circulating air oven overnight.

Cortical and cancellous bone are processed separately. The cortical bone rings are cut into pieces 1 cm wide. The cancellous bone slices are sawed into plates 15 mm square.

The dried bone is transferred to a Soxhlet extractor modified for hot extraction and is extracted for 72 hours with boiling toluene. The degreased bone can be stored after drying at 80° C. in closed containers.

(b) Preparation of Granular Bone Mineral 1700 g degreased cortical bone, 1000 ml 99% ethylene diamine and 150 ml deionized water are heated under reflux in an Erlenmeyer flask immersed in an oil bath for a period of 50 hours. Boiling begins at 115° C. The temperature of the boiling mixture rises to 119° C. towards the end of the treatment.

After cooling, the reddish-brown amine reagent is decanted, and the bones re-rinsed three times with cold, deionized water.

The bone material is transferred to a glass cylinder fitted with a fritted glass support near the bottom. A continuous flow of water is passed through the porous glass disk and the layer of bone material.

The crude bone mineral is dried at 100° C. in a circulating air oven and ground on a roller mill to particle size below 2 mm.

The above-described amine treatment is repeated in exactly the same way using the pretreated material, but the subsequent washing is extended to 15 days.

The resulting bone mineral is dried at 160° C. and then heated to 350° C. in a porcelain pan for 20 hours.

1102 g of white granular, pure bone mineral are obtained. The material can be separated by sieving into fractions of more uniform particle size.

Example 2—Preparation of Cancellous Bone Mineral

Principally the same methods described in Example 1(b) are used. 600 g degreased cancellous bone plates from Example 1(a), 1500 ml 99% ethylene diamine and 75 ml deionized water are heated under reflux for 50 hours. The treated bone is washed with water during 6 days.

The wet bone is subjected to a second similar treatment with 1500 ml ethylene diamine, an addition of water being omitted. The subsequent washing is prolonged to 17 days.

The final drying and heat treatment at 350° C. is performed in exactly the same way as described in Example 1(b).

366 g of pure, white, extremely friable, cancellous bone mineral are produced.

Example 3—Preparation of Cortical Bone Mineral Pieces 700 g degreased cortical bone pieces are treated with ethylene diamine/water mixture as described in Example 1(b) and washed during 6 days.

The wet raw bone mineral is subjected to a second similar treatment using 1000 ml ethylene diamine and 50 ml water, followed by a 10 day water washing.

To achieve highest purity, the wet bone mineral pieces are boiled 5 days in 1 liter pure ethylene diamine and then extracted in a slow stream (1 liter/hour) of cold deionized water for 22 days.

The product is finally dried overnight at 160° C. and then heated to 400° C. during 25 hours.

1085 g of faintly reddish, brittle bone mineral pieces are yielded. Eventual organic contaminations could not be detected, their concentration being below the analytical detection limit.

Example 4

Granular bone mineral with a particle size between 1 and 2 mm was prepared using the procedures describe in Example 1. The material was characterised by electron microscopy, X-ray diffractography and mercury porosimetry. Each of these methods measures a different property of the material. Using electron microscopy it was found, that the material consists of crystalline platelets about 200 to 400 Å units in size (20 to 40 nm). Their thickness appear to be at most 100 Å units (10 nm), since the crystals are still permeated by the electrons. The crystal size distribution seems to be rather narrow, but due to the insufficient disagglomeration a more quantitative evaluation was not feasible. FIG. 1 is an electron micrograph of the bone mineral of the invention at a magnification of 100,000.

By X-ray diffractography it was found, that the material had pure hydroxyl apatite crystal structure. No interferences of other lattice structures was observed. Using the Laue-Scherrer relation the average crystal size in the 002-direction could be estimated to 315 Å units (31.5 nm) with confidence limits of 276 and 362 Å units (27.6 and 36.2 nm).

Mercury porosimetry up to a pressure of 1000 atm yielded the following figures:

| Pore Volume: | 0.249 cm3/g |
|---|---|
| Inner Surface: | 41.700 m2/g |
| Most Frequent Pore Diameter: | 18 nm |

When the measurement was discontinued at 1000 atm the pore volume still rose with pressure. This means, that the material contains pores with diameters below 150 Å units (15 nm), that were not penetrated earlier. The pore volume and inner surface given above should therefore be considered as lower limits.

Example 5—High Temperature Treatment

Samples of the described material were heated for 18 hours to temperatures between 600° C. and 800° C. in an electric furnace and were then analysed in the same way as he original product. The results are summarised in Table 1 hereinafter.

With rising heating temperature the crystals and the pores grow larger while the inner surface shrinks.

After heating to 600° C. the small pores with diameters less than 15 nm have disappeared in favour of larger pores.

After heating 650° C. a very wide crystal size distribution and two predominant pore sizes with diameters of 34 nm and 130 nm are observed.

Raising the temperature from 700° C. to 800° C. decreases the pore volume abruptly from 0.216 cm3/g to 0.042 cm3/g probably due to the commencement of sintering.

Heating in the above temperature range used causes crystal growth but no change in the crystal lattice structure. This could be independently confirmed by thermodiffractography: At about 650° C. the formerly broad interferences rapidly become sharp without changing their directions.

TABLE 1

MODIFICATION OF CRYSTAL SIZE AND POROSITY BY HEAT TREATMENT

| | | x-ray Diffractography | | | Mercury Porosimetry | | |
|---|---|---|---|---|---|---|---|
| Sample heated 18 hrs. to | Electron Microscopy crystal size approx. (nm) | crystal size 002 (nm) | confidence limits (nm) | (nm) | pore volume (cm3/g) | inner surface (m2/g) | most frequent pore diameter (nm) |
| no heating | 10 × 20 × 40 | 31.5 | 27.6 | 36.2 | >−0.249 | >41.7 | 18 |
| 600° C. | 10 × 30 × 60 | 30.7 | 27.6 | 33.9 | 0.318 | 36.3 | 32 |
| 650° C. | 20 to 250 | 47.7 | 41.6 | 54.4 | 0.282 | 17.7 | 34 + 130 |
| 700° C. | 100 to 300 | 59.6 | 48.9 | 69.9 | 0.216 | 5.2 | 160 |
| 800° C. | 100 to 400 | 61.2 | 52.0 | 69.9 | 0.042 | 1.1 | about 200 |

We claim:

1. A bone mineral for use in medicine derived from natural bone and retaining substantially the original crystal structure and mineral microstructure of natural bone permitting physiologically controlled, cell mediated remodelling on implantation, while having an organic impurity content below 150 parts per million and a protein content below 135 parts per million.

2. A bone mineral as claimed in claim 1 which has absorbed thereon a therapeutic amount of one or more antibiotics, sulphonamides or condensation products of formaldehyde and taurinamide.

3. A bone mineral as claimed in claim 1 or claim 2 having adsorbed thereon a therapeutic amount of one or more mitogenic, morphogenic, angiogenic factors and-/or transforming growth factors.

4. A method of bone implantation or bone replacement, comprising forming a remodelling implant or a prosthetic bone replacement from bone mineral as claimed in claim 1, and surgically introducing the remodelling implant or prosthetic bone replacement into a patient.

* * * * *

UNITED STATES PATENT AND TRADEMARK OFFICE
CERTIFICATE OF CORRECTION

PATENT NO. : 5,417,975
DATED : May 23, 1995
INVENTOR(S) : Heinz Lussi et al

It is certified that error appears in the above-indentified patent and that said Letters Patent is hereby corrected as shown below:

Column 6, line 41, "700 g" should be -- 1700 g --;

Column 6, line 60, "describe' should be --described --.

Signed and Sealed this

Eighteenth Day of July, 1995

Attest:

BRUCE LEHMAN

*Attesting Officer*        *Commissioner of Patents and Trademarks*